US009609873B2

(12) United States Patent
Borrelli et al.

(10) Patent No.: US 9,609,873 B2
(45) Date of Patent: *Apr. 4, 2017

(54) COATED, ANTIMICROBIAL, CHEMICALLY STRENGTHENED GLASS AND METHOD OF MAKING

(71) Applicant: CORNING INCORPORATED, Corning, NY (US)

(72) Inventors: Nicholas Francis Borrelli, Elmira, NY (US); David Lathrop Morse, Corning, NY (US); Wageesha Senaratne, Horseheads, NY (US); Florence Christine Monique Verrier, Corning, NY (US); Ying Wei, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 46 days.

This patent is subject to a terminal disclaimer.

(21) Appl. No.: 14/590,242

(22) Filed: Jan. 6, 2015

(65) Prior Publication Data
US 2015/0118276 A1 Apr. 30, 2015

Related U.S. Application Data

(66) Continuation of application No. 13/197,312, filed on Aug. 3, 2011, now Pat. No. 8,973,401, Substitute for application No. 61/510,245, filed on Jul. 21, 2011.
(Continued)

(51) Int. Cl.
*C03C 4/00* (2006.01)
*A01N 59/16* (2006.01)
(Continued)

(52) U.S. Cl.
CPC ............. *A01N 59/16* (2013.01); *A01N 25/08* (2013.01); *C03C 4/00* (2013.01); *C03C 17/30* (2013.01);
(Continued)

(58) Field of Classification Search
None
See application file for complete search history.

(56) References Cited

U.S. PATENT DOCUMENTS

| 3,549,344 A | 12/1970 | Loukes et al. ............... 65/60.13 |
| 3,798,013 A | 3/1974 | Inoue et al. ................ 65/30.14 |

(Continued)

FOREIGN PATENT DOCUMENTS

| DE | 102005039298 A1 | 2/2007 |
| EP | 0250635 | 12/1990 |

(Continued)

OTHER PUBLICATIONS

Veron et al., "Luminescence Study of Silver Nanoparticles Obtained by Annealed Ionic Exchange Silicate Glasses", Plasmonics, Mar. 2010, pp. 213-219.*

(Continued)

*Primary Examiner* — Lisa Herring
(74) *Attorney, Agent, or Firm* — Jie Gao

(57) ABSTRACT

The disclosure is directed to a chemically strengthened glass having antimicrobial properties and to a method of making such glass. In particular, the disclosure is directed to a chemically strengthened glass with antimicrobial properties and with a low surface energy coating on the glass that does not interfere with the antimicrobial properties of the glass. The antimicrobial has an Ag ion concentration on the surface in the range of greater than zero to 0.047 μg/cm². The glass has particular applications as antimicrobial shelving, table tops and other applications in hospitals, laboratories and (Continued)

other institutions handling biological substances, where color in the glass is not a consideration.

19 Claims, 5 Drawing Sheets

Related U.S. Application Data

(60) Provisional application No. 61/371,364, filed on Aug. 6, 2010.

(51) Int. Cl.
*C03C 17/30* (2006.01)
*C03C 21/00* (2006.01)
*A01N 25/08* (2006.01)

(52) U.S. Cl.
CPC .......... *C03C 21/002* (2013.01); *C03C 21/005* (2013.01); *C03C 2204/02* (2013.01); *C03C 2204/04* (2013.01); *C03C 2217/76* (2013.01); *Y10T 428/24926* (2015.01); *Y10T 428/265* (2015.01); *Y10T 428/27* (2015.01); *Y10T 428/273* (2015.01); *Y10T 428/315* (2015.01); *Y10T 428/31612* (2015.04)

(56) References Cited

U.S. PATENT DOCUMENTS

| | | | |
|---|---|---|---|
| 4,902,330 A | 2/1990 | Sakai et al. | |
| 5,078,772 A | 1/1992 | Asahara et al. | 65/30.13 |
| 5,151,958 A | 9/1992 | Honkanen | 385/50 |
| 6,183,558 B1 | 2/2001 | Otake et al. | 118/65 |
| 7,232,777 B1 | 6/2007 | Hyning | |
| 8,869,558 B2 | 10/2014 | Yamamoto et al. | |
| 2003/0097858 A1 | 5/2003 | Strohhofer et al. | |
| 2007/0003603 A1 | 1/2007 | Karandikar et al. | |
| 2007/0172661 A1* | 7/2007 | Fechner | A01N 59/16 428/409 |
| 2009/0041984 A1* | 2/2009 | Mayers | C03C 17/007 428/141 |
| 2009/0142568 A1 | 6/2009 | Dejneka et al. | 428/220 |
| 2009/0202817 A1* | 8/2009 | Durandeau | B05D 1/62 428/332 |
| 2009/0220761 A1 | 9/2009 | Dejneka et al. | |
| 2010/0009154 A1 | 1/2010 | Allan et al. | |
| 2010/0028607 A1 | 2/2010 | Lee et al. | |
| 2010/0035038 A1 | 2/2010 | Barefoot et al. | |
| 2011/0081542 A1 | 4/2011 | Pilloy et al. | |
| 2011/0305874 A1* | 12/2011 | Thoumazet | C03C 17/42 428/172 |
| 2012/0219792 A1 | 8/2012 | Yamamoto et al. | 428/336 |
| 2013/0130023 A1 | 5/2013 | Boulanger et al. | C03C 4/00 |

FOREIGN PATENT DOCUMENTS

| | | | |
|---|---|---|---|
| EP | 1270527 | 1/2003 | |
| EP | 2064220 | 10/2010 | |
| EP | 1828071 | 2/2011 | |
| EP | 2430922 | 3/2012 | |
| JP | 11228186 | 8/1999 | |
| JP | 11319042 | 11/1999 | |
| JP | 11319042 A | 11/1999 | ............... A61L 2/16 |
| JP | 2000-53451 | 2/2000 | |
| JP | 2001-80941 | 3/2001 | |
| JP | 2001080941 A | 3/2001 | |
| JP | 2009295249 A | 12/2009 | |
| JP | 2010138025 A | 6/2010 | |
| JP | 2011-133800 | 7/2011 | |
| KR | 1268956 | 5/2013 | |
| WO | 2005/030665 | 4/2005 | |
| WO | 2006058906 | 6/2006 | |
| WO | 2011065293 | 6/2011 | |
| WO | 2011069338 | 6/2011 | |

OTHER PUBLICATIONS

Nunzio et al., "Silver containing bioactive glasses prepared by molten salt ion exchange", J. of the European Ceramic Society 24 (2004), pp. 2935-2942.*
Patent Cooperation Treaty International Notification of Transmittal of the International Written Opinion of the International Searching Authority, international application No. PCT/US2011/046685: mailing date Oct. 31, 2011, 10 pages.
English Translation of JP2000-53451.
English Translation of WO2011065293.
English Translation of WO2011069338.
Lv et al.; "Antibiotic Glass Slide Coated With Silver Nanoparticles and Its Antimicrobial Capabilities"; Polymers for Advanced Technologies, 2008, 19, 1455-1460.
Nunzio et al.; "Silver Containing Bioactive Glasses Prepared by Molten Salt Ion-Exchange" Journal of the European Ceramic Society, 24, 2004, 2935-2942.
Verne et al.; "Surface Characterization of Silver-Doped Bioactive Glass"; Biomaterials, 26, 2005, 5111-5119.
Verne et al.; Surface Silver-Doping of Biocompativle Glass to Induce Antibacterial Properties. Part I: Massive Glass; J. Mater. Sci: Mater Med, 2009, 20, 733-740.
E. Bradford in "The Great Seige [Malta, 1565]" (New York, Harcourt, Brace & World Inc., 1961, p. 190-191.

* cited by examiner

COATED, ANTIMICROBIAL, CHEMICALLY STRENGTHENED GLASS AND METHOD OF MAKING

CROSS-REFERENCE TO RELATED APPLICATIONS

This application is a continuation of U.S. application Ser. No. 13/197,312, titled "Coated, Antimicrobial, Chemically Strengthened Glass and Method of Making" filed Aug. 3, 2011, which claims benefit of priority under 35 U.S.C. §119 of U.S. Provisional Application Ser. No. 61/371,364 titled "Functionally Coated Antibacterial, Chemically Strengthened Glass and Method of Making" filed Aug. 6, 2010 and U.S. Provisional Application No. 61/510,245 "Functionally Coated, Antimicrobial, Chemically Strengthened Glass and Method of Making" filed Jul. 21, 2011 the content of which are s relied upon and incorporated herein by reference in their entirety.

FIELD

The disclosure is directed to a chemically strengthened glass having antimicrobial properties and method of making such glass. In particular, the disclosure is directed to a colorless transparent chemically strengthened glass with antimicrobial properties and with a functional coating on the glass that does not interfere with the antimicrobial properties of the glass.

BACKGROUND

The "health properties" of metallic silver (that is, its antiseptic, antibacterial, antiviral, antimicrobial effects) was known for centuries before knowledge of bacteria, viruses and microbes generally even existed. In antiquity (Hippocrates of Cos and Galen of Pergamum, both physicians), and well through the Middle Ages, silver vessels were used in the care of those who were ill and wounded. For example, E. Bradford in "*The Great Siege* [Malta, 1565]" (New York, Harcourt, Brace & World Inc., 1961, pp. 190-191) describes the practices of the Knights of the Order of St. John, who were hospitalers, at Malta as:

"Simple though their surgery was and ignorant though they were in many ways, they did at least understand the rudiments of hygiene. In the hospital, where under normal conditions both rich and poor, Knight and commoner, were served off silver plate—to increase "the decorum of the hospital and the cleanliness of the sick"—some attempt was made, even during the siege, to look after the patients properly." [Emphasis added. Internal quotation from Francisco Balbi de Correggio, "*La verdadera relación de todo lo que el ano de MDLXV ha succedido en la Isla de Malta*,' (Barcelona, 1568)].

It was later discovered that the actual bactericide was not the metallic silver, but the silver ions on the surface of the bulk metallic silver. Thus, the beneficial effect of using silver vessels may be attributable to the migration of silver ions from the bulk silver to the food and drink that was consumed. With the knowledge that silver ions were are actual "antiseptic," solutions of certain silver salts (e.g. silver nitrate) that are readily soluble in water were used as an antiseptic and bactericide for many decades. Until the 1980s, dilute silver nitrate eye drops were placed in the eyes of newborns to prevent neonatal conjunctivitis, which could lead to blindness in the newborn, which may occur after birth. (This practice has generally been discontinued in favor of the use of erythromycin ointment).

Recently, the use both metallic silver particles and silver salts have been described in the patent and technical literature as a means for imparting antibacterial properties to a variety of materials such as yarns, fabrics, glass and other materials. Yahoo Lv et al. (Polymers for Advanced Technologies, Vol. 19 (1008), pages 1455-1460) have shown that silver ($Ag^0$) nano-particles coated on a glass slide have antibacterial/antiviral properties resulting from close attachment of the nano-particles with the bacterial cells. The principle activity of silver (0) particles is due to the production of silver ions within an aqueous matrix containing the bacteria. Di Nunzio et al in WO 2006/058906 describe prosthetic devices or implants having at least a surface layer or a part thereof (that is, an element of the prosthetic device or implant) made of a glass, glass-ceramic or ceramic material containing ions exchangeable with silver ions, and subjecting the device "to a silver ion containing aqueous solution ion-exchange process," [id at the Abstract]. Di Nunzio et al., J. European Ceramic Society Vol. 24 (2004), pages 2935-2942, discuss bioactive glasses containing silver on their surface that were produced by ion-exchange from dilute silver nitrate melts. Verne et al, J. Material Science; Materials Medicine Vol. 20 (2009), pages 733-740, present test results of the surface doping of biocompatible glass that was described in WO 2006/058906. U.S. Pat. No. 7,232,777 describes yarns and fabrics having an antimicrobial silver particulate finish.

Silver ions do not possess a single mode of action. They interact with a wide range of molecular processes within microorganisms resulting in a range of effects from inhibition of growth and loss of infectivity to cell death (cytotoxicity). The mechanism depends on both the concentration of silver ions that are present and the sensitivity of the microbial species to the silver ions. Contact time, temperature, pH and the presence of free water all impact on both the rate and extent of antimicrobial activity. However, the spectrum of activity is very wide and the development of resistance relatively low, especially in clinical situations. Silver ions are known to be effective against some 650 types of bacteria.

The prevalence of "touch screens" in contemporary society gives rise to many surfaces that can harbor microbes, bacteria and viruses, and these microbes can be transferred from person to person. The present disclosure is directed to glass surfaces and to the application of the antimicrobial properties of silver ions to glasses such as the cover glasses used on many modern devices, for example, ATMs, touch screen computers, cellphones, electronic book readers, and similar devices.

SUMMARY

This disclosure is directed to a making a chemically strengthened glass having antimicrobial properties and to methods of making such glass. In one embodiment the disclosure is directed to a colorless transparent chemically strengthened glass with both antimicrobial properties and a functional coating on the glass that does not interfere with the properties of the glass. The functional coating is used to impart easy cleanability to the surface and is generally a hydrophobic coating. The task of creating a chemically strengthened glass having antimicrobial properties and having a functional coating on the glass is not straightforward due to the fact that there are numerous other required properties of the cover glass that must be maintained while trying to incorporate the antimicrobial property. It should also be understood that the interaction of the Ag-ion with the bacteria is restricted to the surface of the glass, so the pertinent characterization of the concentration needs to be expressed as per unit area. The reporting of the volume concentration at some interior point away from the surface, for example, >5 nm is of little consequence since the mobility of $Ag^{+1}$ at room temperature is negligible.

Another embodiment the disclosure is directed to a method of making a chemically strengthened glass having silver ions ($Ag^{+1}$) on the surface of the glass. There have been proposals to utilize a one-step (1-step) method in which an ion-exchange bath containing both a silver compound and an ion-exchanging alkali metal compound whose ions are larger than the alkali metal ions in the article into which they be exchanged, and using such bath exchange both Ag ions and the larger ions into the glass in a single step to form a chemically strengthened, silver containing glass having a compressive stress. For example, in addition to the silver ions, the alkali metal ions that are exchanged into the glass are potassium ions ($K^{+1}$). Prior art and our experiments show that the 1-step ion-exchanging bath consisting of potassium nitrate containing silver nitrate in an amount in the range of 0.01 wt % to 5 wt % where the ion exchange temperatures are typically at 300-500° C. with ion exchange times of >3 hours exhibits distinct disadvantages. The most significant disadvantage is that to enhance the "kill" rate of bacteria and other microbes it is necessary that there be a sufficiently a high concentration of Ag-ion on the surface which is not achieved through the use a one-step process; and further when the 1-step method is used significant color is produced as a consequence. This color makes the glass unsuitable for use in electronic devices by altering the display, for example, by making it less clear or altering the colors.

Disclosed herein is a two-step (2-step) method that avoids the disadvantages of the 1-step method. The 2-step method uses a first ion-exchange bath containing an ion-exchanging alkali metal compound whose ions are larger than the alkali metal ions in the article into which they will be exchanged (the standard strengthening method on chemical strengthening), followed by ion-exchange using a second ion-exchange bath containing silver, the second silver-containing ion-exchange bath being used for a much shorter time than the first bath. The second ion-exchange bath contains a high concentration of both silver ions and an ion-exchanging alkali metal compound whose ions are larger than the alkali metal ions in the article into which they be exchanged, the silver ion concentration in the second bath being higher than that used in the in the silver-containing bath of the 1-step method. In the first step, the larger alkali metal ions are exchanged into the glass to form a glass article having a compressive stress in the usual manner for a time greater than 3 hours at a temperature in the range of 300-500° C.; for example, by ion-exchange at 420° C. for 5-6 hours. In the second step, the higher concentration of silver ions are exchanged into the surface of the glass and replace the alkali metal ions in the glass to a shallow enough depth without significant loss of compressive stress. In one embodiment of the 2-step method, the same alkali metal compound can be used in both the first and second ion-exchange baths. In certain embodiments of the 2-step method the silver compound and alkali metal compound used in the ion-exchange bath are both comprised of nitrates. Furthermore, the potassium ions are typically ion-exchanged for sodium and lithium alkali metal ions in the glass.

Generally, the 2-step method comprises providing a glass article containing ion-exchangeable alkali metal ions, providing a first ion-exchange bath containing ion-exchanging alkali metal compound whose ions are larger than the alkali metal ions in the article, and, as a first step, ion-exchanging the alkali metal ions in the glass for the alkali metal ions in the ion-exchange bath. As a second step, the method further comprises providing a second ion-exchange bath containing silver nitrate in an amount in the range of 1-10 wt %, the remainder of the bath being the nitrate of the an alkali metal ion having ion larger than the alkali metal ions at least equal in size to the alkali metal ions of the first ion-exchange bath. In one embodiment, the duration of the second bath exposure, that is, the ion-exchange time using the second bath, is less than 30 minutes in order to produce a shallow depth of exchange of less than 20 µm. In another embodiment the ion-exchange time is greater than zero and less than or equal to 20 minutes. In an additional embodiment, the ion-exchange time is greater than zero and less than or equal to 10 minutes. In all embodiments, the ion-exchange is carried out at a temperature in the range of 370° C. to 450° C. using a selected ion exchange time as described herein. In one embodiment, the ion exchange is carried out at a temperature in the range of 400° C. to 440° C. using a selected ion exchange time as described herein. The distinct advantage of the 2-step method is that since only the surface concentration of $Ag^{+1}$ is important for the antimicrobial effect, having the silver penetrate to greater depths as is achieved through the 1-step method adds nothing to the antimicrobial or antibacterial effect since silver ions do not move or migrate within the glass at temperatures at which electronic devices may be used; temperatures which typically range from below 0° C. to as high as 45° C. or higher. The 2-step method thus allows one to obtain a significantly higher concentration of $Ag^{+1}$ ions on the surface of the glass which results in a commensurate decrease in the "kill" time (the time to reach a log 3 reduction) while not producing any undesirable yellow color and therefore achieving the desirable transmittance characteristics as is shown in FIG. 1.

FIG. 1 compares the transmission in the 400-750 nm range of an antimicrobial glass ion-exchanged for 20 minutes using the 2-step method with an antimicrobial glass prepared by the 1-step method using the same ion-exchange bath for 5 hours. The glass of the 2-step method has a transmission, uncorrected for reflection losses, of greater than 88% over the entire range whereas the glass prepared by the 1-step method is less than 88% in the range of 400 mm to approximately 560 nm and equal to or greater than 88% only in the range of approximately 560 nm to 750 nm.

As mentioned above, the 2-step method, by restricting the second step to very short times, <30 minutes, one can produce a high concentration of $Ag^{+1}$ on the surface without imparting any color. In fact the silver ion concentration on the surface is larger for the short IOX time of the 2-step method compared to the longer IOX time (typically 4-6 hours) of the 1-step method. The volume concentration of Ag ion in the first 5 nm of the glass can be determined using XPS (x-ray photoluminescence-spectroscopy. Tables 1 and 2 show the XPS results for the Ag ion concentration in the first 5 nm of the glass.

TABLE 1

| 1-step Ion-Exchange | |
|---|---|
| Sample No | Ag concentration, Atomic % |
| 1 | 1.85 |
| 2 | 1.55 |

TABLE 1-continued 1-step Ion-Exchange

| Sample No | Ag concentration, Atomic % |
|---|---|
| 3 | 1.86 |
| 4 | 1.94 |
| average | 1.80 |
| 95% uncertainty | 0.28 |

All samples ion-exchanged using the 1-step method and a 5 wt % AgNO$_3$/95 wt % KNO$_3$ bath at 420° c. for 5.5 hours

TABLE 2

2-step Ion-Exchange

| Sample No | Ag concentration, Atomic % |
|---|---|
| 1 | 2.68 |
| 2 | 1.97 |
| 3 | 2.22 |
| 4 | 3.22 |
| Average | 2.52 |
| 95% uncertainty | 0.90 |

All samples were ion-exchanged using the 2-step method and a second step 5 wt % AgNO$_3$/95 wt % KNO$_3$ bath at 420° c. for 20 minutes A comparison of the Tables 1 and 2 shows that the glass prepared by the 2-step method, 20 minute IOX time for the second bath, has a 40% increase in the Ag ion concentration in the first 5 nm relative to the Ag ion concentration in the glass produced by the 1-step, single bath process, 5% AgNO$_3$/95% KNO$_3$ bath being used in both processes.

Another aspect the present disclosure is the ability to produce a glass that has an antimicrobial surface that is easily cleanable without the loss of the antimicrobial activity. A "low surface energy" coating is applied to the surface of the silver-containing, chemically strengthened antimicrobial glass to impart easy-to-clean properties to the glass surface. The low surface energy coating is a hydrophobic coating that facilitates the ease of cleanability of the surface. In one embodiment, the low surface energy coating has a thickness in the range of 0.5 nm to 20 nm. In another embodiment, the low surface energy coating is a continuous coating and has a thickness in the range of 0.5 nm to 10 nm. In a further embodiment, the film is continuous and has a thickness in the range of 0.5 nm to 5 nm. In an additional embodiment, the thickness is in the range of 1 nm to 5 m. In an additional embodiment, the film is continuous and has a thickness in the range of 1 nm to 5 nm. In another embodiment, the low surface energy coating can form a pattern or domains on the surface, for example without limitation, "islands-in-the-sea" where the silver-containing, chemically strengthened surface of the glass is the sea and the low surface energy coating forms the islands. Stated another way, the low surface energy coating is discontinuous and does not cover every portion of the glass surface, but does cover a sufficient portion of the surface such that the coating is effective for its intended antimicrobial use and for its use in facilitating ease of cleanability. Such discontinuous coating can also vary in thickness over the range of 0.5 nm to 20 nm. In one embodiment, the discontinuous coating has a thickness in the range of 0.5 nm to 10 nm. In an additional embodiment, the discontinuous coating has a thickness in the range of 1 nm to 5 nm. In a still further embodiment, the coating can be a continuous "peak-to-valley" ("PV") coating where the coating "peak" is thicker than the coating "valley". For example, within the range of 0.5 nm to 20 nm, the coating within the "peak" can be in the range of 15 nm to 20 nm and the coating within the "valley" areas can be, for example, in the range of 1 nm to 5 nm. The selected depth to which the Ag$^{+1}$ ions are deposited may vary according to the silver concentration in the IOX bath, the temperature of the bath and the time for which the ion-exchange of the silver ions into the glass was carried out.

In one embodiment, the surface of the glasses described herein having antimicrobial activity and exhibiting a surface Ag ion concentration of greater than zero to 0.05 μgAg/cm$^2$, are not cytotoxic. In another embodiment, the non-cytotoxic glass has a surface Ag ion concentration in the range of 0.005 μgAg/cm$^2$ to 0.047 μgAg/cm$^2$. In an addition embodiment the non-cytotoxic glass has a surface Ag ion concentration in the range of 0.005 μgAg/cm$^2$ to 0.035 μgAg/cm$^2$. In a further embodiment, the non-cytotoxic glass exhibits a surface concentration in the range of 0.01 μg/cm$^2$ to 0.030 μg/cm$^2$. In an additional embodiment the surface concentration of the non-cytotoxic glass is in the range of 0.015 μg/cm$^2$ to 0.03 μg/cm$^2$.

DETAILED DESCRIPTION

Figure 1:
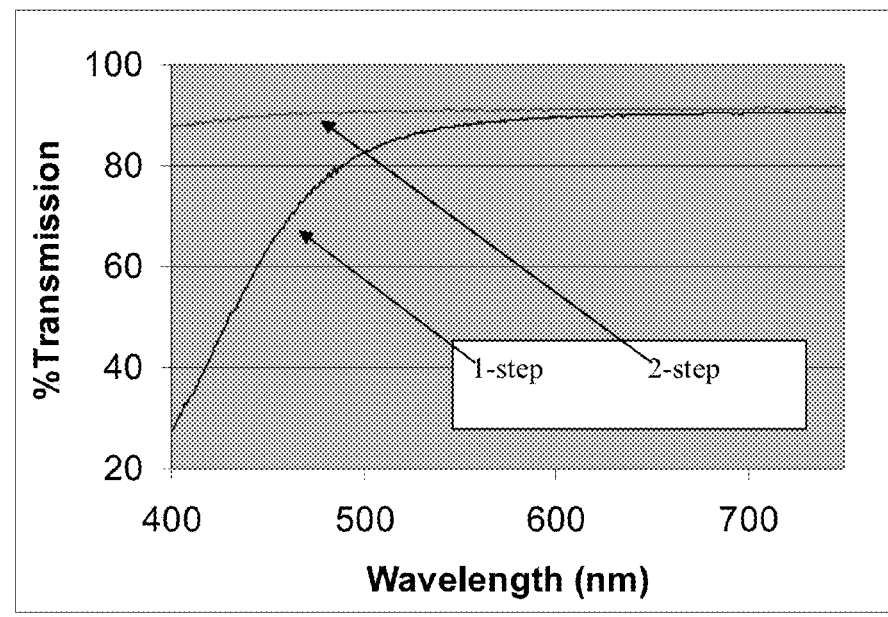
FIG. 1 is a graph of the optical transmission (not corrected for reflection losses) comparing the results from the 1-step process (5 wt % AgNO$_3$ in KNO$_3$, 5.5 hours, 420° C.) for incorporating Ag ions into a glass with the 2-step process (100 wt % KNO$_3$, 420° C., 5.5 hours, followed by 5 wt % AgNO$_3$ in KNO$_3$, 95 wt % KNO$_3$, 20 minutes, 420° C.) for Ag ion incorporation into a glass.

As used herein the term "antimicrobial," means an agent or material, or a surface containing the agent or material that will kill or inhibit the growth of microbes from at least two of families consisting of bacteria, viruses and fungi. The term as used herein does not mean it will kill or inhibit the growth of all species microbes within such families, but that it will kill or inhibit the growth or one or more species of microbes from such families. The components of all the glass compositions suitable for ion-exchange are given in terms of weight percent (wt %) as the oxide unless indicated otherwise. The surface concentration of antimicrobial silver ions is given in μg/cm$^2$ and refers to the concentration on the surface of the glass, and not to silver ions "near" or "close to" the surface. Also herein the term "2-step method" includes not only the glass compositions recited herein, but also any glass composition, from any source, that is suitable for chemical strengthening by ion-exchange to impart a compressive stress to the glass, or any glass that may have been chemically strengthened for another purpose and is used to prepare an antimicrobial glass according to the second step of the 2-step method.

As used herein the term "Log "Reduction" or "LR" means Log $(C_a/C_0)$, where $C_a$=the colony form unit (CFU) number of the antimicrobial surface containing silver ions and $C_0$=the colony form unit (CFU of the control glass surface that does not contain silver ions. That is:

$$LR=-\text{Log}(C_a/C_0),$$

As an example, a Log Reduction of 4=99.9% of the bacteria or virus killed and a Log Reduction of 6=99.999% of bacteria or virus killed.

As used herein the term "low surface energy coatings" are hydrophobic coatings, for example without limitation, (a) $(RO)_{4-z}$—Si—$[(CH_2)_3$—$OCF_2$—$CF_2$—$[OCF_2$—$CF_2$—$CF_2]_n$—$F]_z$, where z=1 or 2, n is an integer sufficient to provide that $[(CH_2)_3$—$OCF_2$—$CF_2$—$[OCF_2$—$CF_2$—$CF_2]_n$—$F]$ has a length in the range of nm to 20 nm, and RO=$CH_3O$—, $CH_3$—$CH_2O$—, or $CH_3C(O)O$—, and (b) $(RO)_{4-z}$—Si—$[(CH_2)_x$—$(CF_2)_y$—$CF_3]_z$, where x+y are integers whose sum is sufficient to provide that $[(CH_2)_x$—$(CF_2)_y$—$CF_3]$ has a length in the range of 1 nm to 20 nm, with the provision that y≥x, z is 1 or 2, and RO=$CH_3O$—, $CH_3$—$CH_2O$—, or $CH_3C(O)O$—.

The values of n, x and y in the above two formulas can be determined using the covalent radius of carbon and oxygen which are 0.077 nm and 0.073 nm, respectively. The coating has to have a sufficiently long spacer, for example, a plurality of —$CH_2$—, —$CF_2$—, —O—$(CH_2$ and/or $CF_2)_n$ moieties, or combination or such moieties, between the Si atom and the terminal fluorocarbon group, for example, $CF_3$, so that water can contact the glass surface of the glass and transport silver ions from the glass to a microbe. In one embodiment, the total length of the spacer or skeletal chain from the silicon atom and the chain's terminal moiety, for example, $CF_3$, is in the range of 1-20 nm. In another embodiment, the total length is in the range of 2-10 nm. In another embodiment, the total length is in the range of 1-10 nm. The silane coating material is attached to the silver-containing glass's surface by 2 or 3 Si—O bonds.

The methods described herein can be used to make antimicrobial glass samples of any thickness. In one embodiment, for example, for use in electronic devices as a touch screen or a touch screen cover glass, for example without limitation, cell phones, computer (including laptops and slates) and ATMs, the glass typically has a thickness in the range of 0.2 mm to 3 mm. In one embodiment the glass has a thickness in the range of 0.2 mm to 2.0 mm. In a further embodiment, the glass has a thickness in the range of 0.3 mm to 0.7 mm. The exemplary glass samples described and used herein for testing were 0.5 mm thick unless specified otherwise. Other applications include use as table tops or cover top, shelving in refrigerators or for storage shelves or shelf cover in, for example, laboratories, hospitals and other facilities where antimicrobial properties are desired. It should be noted that the glass can be thicker according to the intended use. For example, for a hospital bench top or bench top cover, it may be desirable that the glass have a thickness of greater than 3 mm.

Any glass composition capable of being ion-exchanged can be used in accordance with this disclosure. Such glass compositions typically contain the smaller alkali metal ions, typically Na and Li ions that can be exchanged by larger alkali ions, for example by K, Rb and Cs ions and silver ions. In addition, any glass composition, from any source, that is suitable for chemical strengthening by ion-exchange to impart a compressive stress to the glass, or that may have been chemically strengthened for another purpose, can be used to prepare an antimicrobial glass according to the second step of the 2-step method described herein.

Glass compositions that can be used in practicing this disclosure include, without limitation, soda lime, alkali aluminosilicate and alkali aluminoborosilicate glasses. Examples of glasses that can be used are disclosed in commonly assigned U.S. Patent Application Publication Nos. 2010/0035038, 2010/0028607, 2010/0009154, 2009/0220761 and 2009/0142568, the teaching of which are incorporated herein by reference. Exemplary alkali aluminosilicate glass compositions, particularly the base glass compositions, suitable for ion-exchange using an ion-exchange bath including silver ions include:

(a) 60-70 mol % $SiO_2$; 6-14 mol % $Al_2O_3$; 0-15 mol % $B_2O_3$; 0-20 mol % $Na_2O$; 0-10 mol % $K_2O$; 0-8 mol % MgO; 0-10 mol % CaO; 0-5 mol % $ZrO_2$; 0-1 mol % $SnO_2$; 0-1 mol % $CeO_2$; less than 50 ppm $As_2O_3$; and less than 50 ppm $Sb_2O_3$; wherein 12 mol %≤$Na_2O$+$K_2O$≤20 mol % and 0 mol %≤MgO+CaO≤10 mol %.

(b) 64 mol %≤$SiO_2$≤68 mol %; 12 mol %≤$Na_2O$≤16 mol %; 8 mol %≤$Al_2O_3$≤12 mol %; 0 mol %≤$B_2O_3$≤3 mol %; 2 mol %≤$K_2O$≤5 mol %; 4 mol %≤MgO 6 mol %; and 0 mol %≤CaO≤5 mol %, and wherein 66 mol %≤$SiO_2$+$B_2O_3$+CaO≤69 mol %; $Na_2O$+$K_2O$+$B_2O_3$+MgO+CaO+SrO>10 mol %; 5 mol %≤MgO+CaO+SrO≤8 mol %; ($Na_2O$+$B_2O_3$)–$Al_2O_3$≤2 mol %; 2 mol %≤$Na_2O$–$Al_2O_3$≤6 mol %; and 4 mol %≤($Na_2O$+$K_2O$)–$Al_2O_3$≤10 mol %;

(c) 61 mol %≤$SiO_2$≤75 mol %; 9 mol %≤$Na_2O$≤21 mol %; 7 mol %≤$Al_2O_3$≤15 mol %; 0 mol %≤$B_2O_3$≤12 mol %; 0 mol %≤$K_2O$≤4 mol %; 0 mol %≤MgO≤7 mol %; and 0 mol %≤CaO≤mol %;

(d) 50 mol %≤$SiO_2$≤70 mol %; 8 mol %≤$Na_2O$≤16 mol %; 9 mol %≤$Al_2O_3$≤17 mol %; 2 mol %≤$B_2O_3$≤12 mol %; 0 mol %≤$K_2O$≤4 mol %; 0 mol %≤MgO≤4 mol %; and 0 mol %≤CaO≤0.2 mol %. wherein the alkali metal oxides and the alkaline earth metal oxides are modifiers and the ratio [(mol %≤$Al_2O_3$+mol % $B_2O_3$)÷Σ mol %≤modifiers] is greater than 1, that is:

$$[(\text{mol \%} \; Al_2O_3+B_2O_3)\div\Sigma\text{mol \%}\leq\text{modifiers}]>1; \text{ and}$$

(e) $SiO_2$>50 mol %; 11 mol %≤$Na_2O$≤25 mol %; 7 mol %≤$Al_2O_3$≤26 mol %; 0 mol %≤$B_2O_3$≤9 mol %; 0 mol %≤$K_2O$≤2.5 mol %; 0 mol %≤MgO≤8.5 mol %; and 0 mol %≤CaO≤1.52 mol %.

The alkali aluminosilicate glass and alkali-aluminoborosilicate glasses are substantially free of lithium, meaning any lithium present is as a contaminant, whereas in other embodiments, the alkali aluminosilicate glass is substantially free of at least one of arsenic, antimony, and barium. In other embodiments, the alkali aluminosilicate glass has a liquidus viscosity of at least 130 kilopoise and is down-drawable by those techniques known in the art, for example, but not limited to, fusion-draw processes, slot-draw processes, and re-draw processes. In another embodiment the glass can be made by the float process.

A further example, without limitation, of an alkali aluminosilicate glass that can be used in the present disclosure is one described in the commonly assigned U.S. Patent Application Publication No. 2010/0009154 as having a composition of: 66 mol % $SiO_2$; 14 mol % $Na_2O$; 10 mol % $Al_2O_3$; 0.6 mol % $B_2O_3$; 2.5 mol % $K_2O$; 5.7 mol % MgO; and 0.6 mol % CaO; 0.2 mol % $SnO_2$; and 0.02 mol % $ZrO_2$. The sodium in this glass, and other exemplary glasses, can be exchanged with, in addition to silver ions, potassium, rubidium, or cesium to produce a region of high compressive stress near the surface and a region under central tension in the interior or central region of a glass part. Unless otherwise specified, it is understood that use of the terms "lithium," "sodium," "potassium," "cesium," and "rubidium" herein refers to the respective monovalent cations of these alkali metals. If rubidium and cesium are used in the ion-exchange bath they can then also be exchanged for potassium ions as well as for sodium and/or lithium ions in the glass. In one embodiment, some or all of the sodium and/or potassium in the glass composition as-made can be replaced are replaced by lithium in the glass. The lithium can then be ion-exchanged with silver, sodium, potassium, rubidium, or cesium to obtain a high surface compressive stress and an interior volume under tension. In order to produce surface compressive stress (as opposed to tension), one or more of the ions in the glass must be replaced by an ion in the salt solution that has a higher atomic number; for example, silver and sodium replace lithium in the glass, and silver and potassium replace sodium and/or lithium in the glass.

In the examples of the present disclosure, the chemical strengthening of glasses used as an exemplary cover glass article was accomplished in the first step of the disclosed 2-step ion-exchange process where a larger ion such as $K^{+1}$ (from $KNO_3$) is exchanged for a smaller ions in the glass, for example $Na^{+1}$ or $Li^{+1}$. The base glass, before any ion-exchange, used to prepare the antimicrobial glass sample articles evaluated herein has a composition, in weight percent, falling within the range of 66±2 wt % $SiO_2$, 13±1.5 wt % $Al_2O_3$, 13±3 wt % $Na_2O$, 1.5±0.5 wt % $K_2O$, 4±1 wt % MgO, 0.5±0.2 wt % CaO, less than 1 wt % $SnO_2$, less than 0.8 wt % $ZrO_2$ and less than 0.5 wt % $Fe_2O_3$; and the analyzed specific composition of the base glass actually used to prepare the samples was 66.02 wt % $SiO_2$, 13.6 wt % $Al_2O_3$, 13.7 wt % $Na_2O$, 1.7 wt % $K_2O$, 3.9 wt % MgO, 0.45 wt % CaO,). 44 wt % $SnO_2$, 0.04 wt % $ZrO_2$ and 0.017 wt % $Fe_2O_3$, This first step can also be accomplished independently by the use of a glass that has already been chemically strengthened by ion-exchange, even though such strengthening was carried out for a different purpose, for example, simply providing a chemically strengthened, but not antimicrobial, glass. Thus, the first step of the 2-step method described herein can be accomplished by either means. In the second step of the 2-step method described herein silver ions are exchanged into the glass using a bath containing both silver and potassium ions, present as for example nitrates, where the $AgNO_3$ concentration can be in the range 0.1-10 wt % and the ion-exchange is carried out for a time in the range of 1 minute to less then 30 minutes at a temperature in the range of 370° C. to 450° C.

In the examples described herein, $KNO_3$ was used as the alkali metal in the ion-exchanging salt baths and $AgNO_3$ was used as the source of silver ion. For all the examples, unless specified otherwise, the ion-exchanges were carried out at 420° C. for the time indicated for sample as described herein.

Method of Quantifying the Surface $Ag^{+1}$ Concentration

Figure 4:
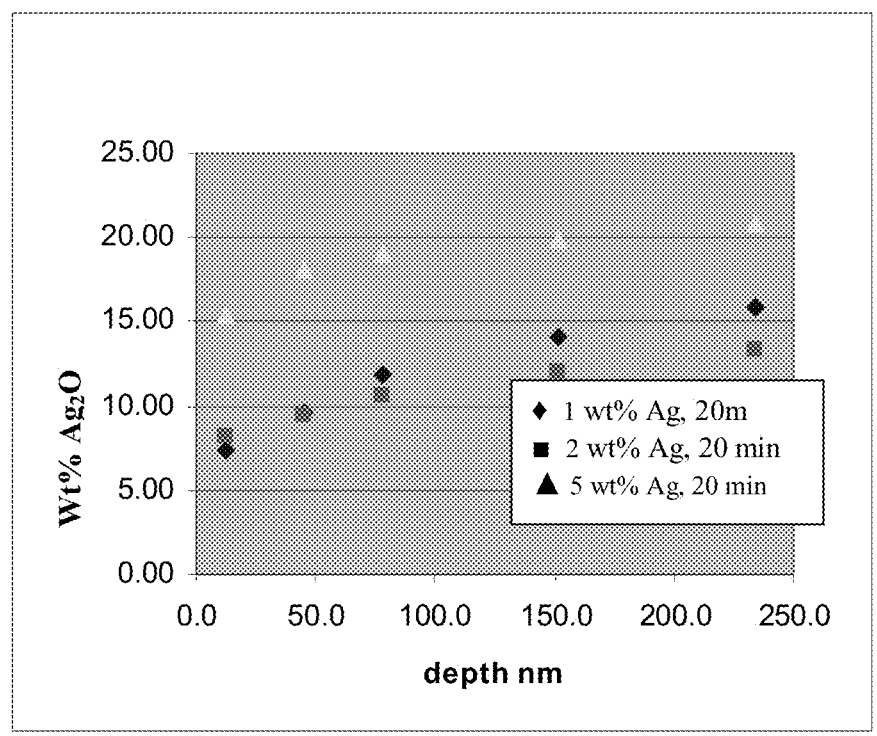
FIG. 4 is graph of EMP results showing the actual silver ion concentration, calculated Ag$_2$O, versus depth for glass samples that were prepared by the 2-step method using different concentrations of AgNO$_3$ in the second bath.

The antibacterial action produced by the silver ions is a "surface effect." In other words, what is important is the nature and extent of the contact of the microbe with the silver-containing surface of the glass. Therefore a quantitative knowledge of the surface $Ag^{+1}$ concentration, in μg/cm$^2$ or ions/cm$^2$, is crucial in ascertaining the effectiveness of the antimicrobial action. This is even more pertinent in the present case where the Ag is being added by an ion-exchange process. The analytical techniques of EMP (electron microprobe) and XPS (X-ray photoluminescence spectroscopy) and SIMS (secondary ion mass spectroscopy) can be used to obtain the $Ag^{+1}$ profile, but they yield volume concentration values, albeit close to the surface, whereas what is important is the surface ion concentration. EMP and XPS can quantitatively determine the $Ag^+$ concentration to within 10-20 nm. TOF-SIMS (time-of-flight secondary ion mass spectroscopy) can look nearer to the surface but it is non-quantitative. What makes the estimate of the surface concentration more difficult is that the $Ag^{+1}$ concentration actually decreases as one nears the surface as shown from the EMP measurements of FIG. 4. FIG. 4 is graph of EMP results showing the actual silver ion concentration, calculated $Ag_2O$, versus depth for glass samples that were prepared by the 2-step method using different concentrations of $AgNO_3$ in the second bath, where the first IOX bath was 100 wt % $KNO_3$ and the second IOX baths were $KNO_3$ baths containing 1 wt % (♦), 2 wt % (■) or 5 wt % (▲) $AgNO_3$, respectively, and the second bath ion-exchange time and temperature were 20 minutes and 420° C., respectively.

The following Table 3 gives the Ag ion bath concentrations, the time for ion-exchange and the resulting EMP measurements, as wt % $Ag_2O$, for several different ion-exchanges. Except for the sample ion-exchanged for 300 minutes, the samples in Table 3 were prepared using the 2-step method. The sample having an ion-exchange time of 300 minutes was prepared by the 1-step method using the same ion-exchange bath having the same composition as the second bath of the 2-step process. All the glass articles of Table 3 have a compressive stress of at least 250 MPa. In one embodiment the compressive stress is at least 500 MPa. In another embodiment the compressive stress is at least 600 MPa. The number term "EMP (15 nm)" refers to a depth which is close as close as the accelerating potential of the method allows. All ion-exchanges of Table 3 were carried out at 420° for both the 1-step sample and the 2-step samples. In the 2-step process the first ion-exchange was done using $KNO_3$ only for a time of 5.5 hours, and the second ion-exchange was done using an $AgNO_3/KNO_3$ bath. The Ag/K bath compositions are given in Table 3.

TABLE 3

| Ag wt % in bath | IOX time, minutes | EMP (≅15 nm), wt % |
|---|---|---|
| 0.15* | 20 | 0.82 |
| 0.15‡ | 330 (5.5 hours) | 1.0 |
| 0.25* | 20 | 1.0 |
| 0.5* | 20 | 2.2 |
| 1.0* | 20 | 5-7 |
| 2.0* | 20 | 7.1-8.1 |
| 5.0* | 20 | 12.3-15.3 |
| 10.0* | 10 | 23-25 |

Figure 5:
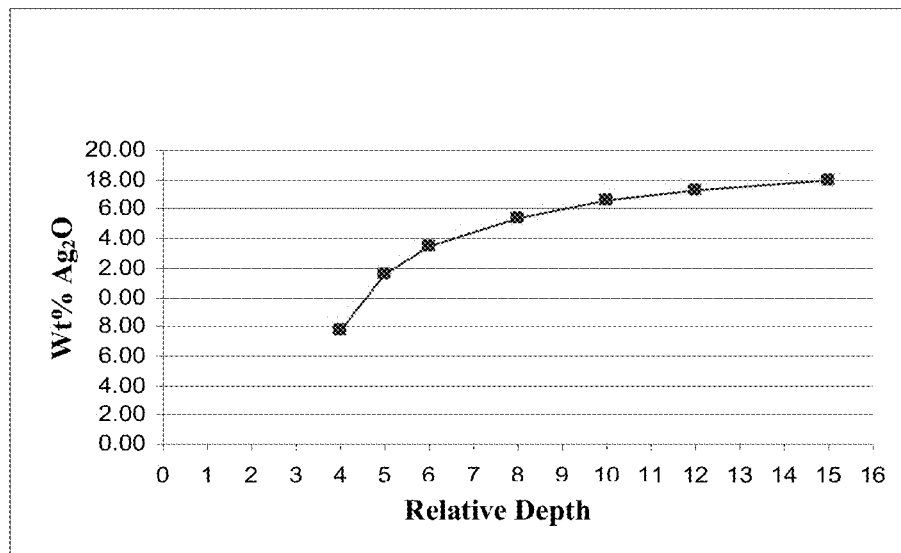
FIG. 5 is a graph of EPM results illustrating the decrease in Ag ion concentration as one proceeds from the center of the glass to the surface of the glass.

Wt % was calculated as the oxide, $Ag_2O$
*= made using the 2-step process
‡= made using the 1-step process The EMP method used was to vary the accelerating potential to access different depths in the glass samples. The glasses of FIG. 5 are the measured values of the wt % $Ag_2O$ vs. depth as a function of the $AgNO_3$ bath concentration in the $2^{nd}$ step of the 2-step process described above.

XPS (x-ray photoluminescence spectroscopy), was also used to estimate the Ag concentration. Although XPS is usually referred to as a surface measurement, it actually measures to a depth 5-10 nm, with approximately 95% of the signal coming from ≤5 nm of the surface. Therefore XPS data should also be interpreted in a way similar to that used to interpret the EMP while data recognizing that the XPS data is from an area closer to the surface of the glass. The XPS results are reported as an atomic percent of the atoms on the surface of the glass substrate and are shown in Table 4. Table 4 also includes the EMP results for the same samples that were XPS analyzed. In Table 4 the samples showing an ion-exchange time of 5.5 hours were prepared using the 1-step method. The sample having an ion-exchange time of 20 minutes was prepared using the 2-step method AG IOX was carried out in the second step.

TABLE 4

Comparison of Ag concentration from XPS and EMP estimates

| Ag Wt % in Bath | IOX Time at 420° C. | $Ag^{+1}$ At % XPS | $Ag_2O$ Wt % XPS (calc) | $Ag_2O$ Wt % EMP | $N/cm^3$ |
|---|---|---|---|---|---|
| 0.1‡ | 5.5 hours | 0.98 | 2 | 2 | $2 \times 10^{20}$ |
| 5%* | 20 minutes | 9.2 | 19 | 19 | $2.28 \times 10^{21}$ |
| 5%‡ | 5.5 hours | 12.6 | 26 | 24 | $3.00 \times 10^{21}$ |

*= 2-step method
‡= 1-step method

The agreement in the amount of $Ag_2O$ is excellent, thus indicating that both methods are measuring the same volume concentration.

While the data presented above provides estimates of the volume concentration, the following paragraphs describe how to determine the actual surface concentration since this is the relevant number pertaining to antimicrobial behavior. Silver in the body of the glass below the surface plays no antimicrobial role since it has no access to the bacteria on the surface.

Determination of the surface concentration can also be done using a statistical method. The relationship is simply derived from the idea of an array of particles N along a line defined as N/cm. Extending this array this to a plane gives one surface concentration $N^2/cm^2$, and similarly extending it to a cube provides a volume concentration $N^3/cm^3$. The fact that the array is disordered is not a limitation as long as one can define an average. In other words, an isotropic homogeneous array of particles allows an average number of particles per unit dimension to be defined. This approach allows one to define the relationship between the surface concentration and the volume concentration as shown in the following Equation 1.

$$N/cm^2 = [N/cm^3]^{2/3} \qquad \text{Eq. 1}$$

Figure 6:
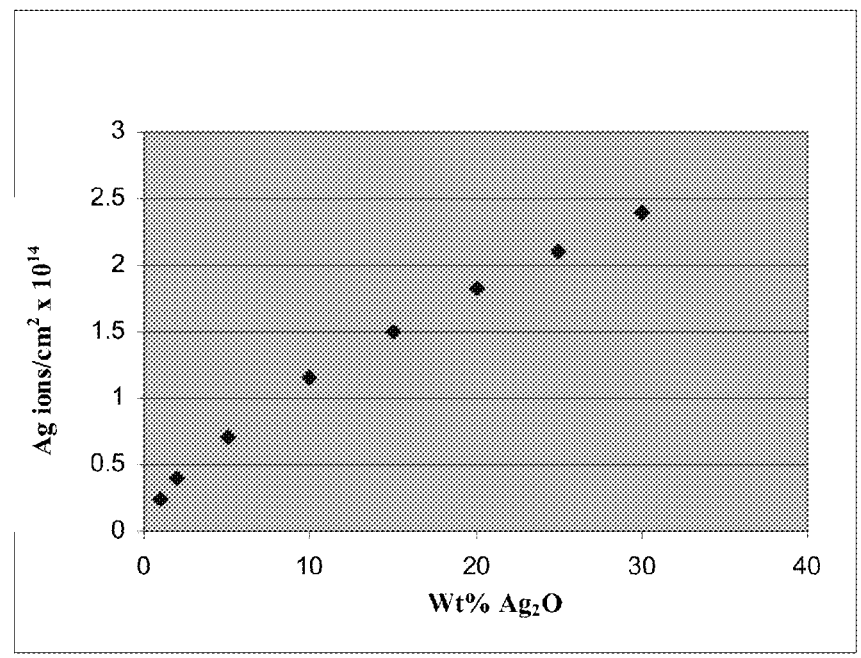
FIG. 6A is a graph illustrating Ag ion surface concentration in ions/cm$^2$×10$^{14}$ versus wt % Ag$_2$O.
FIG. 6B is a graph of a graph of the Ag surface concentration in μg/cm$^2$ versus the wt % Ag$_2$O.
Figure 6B:
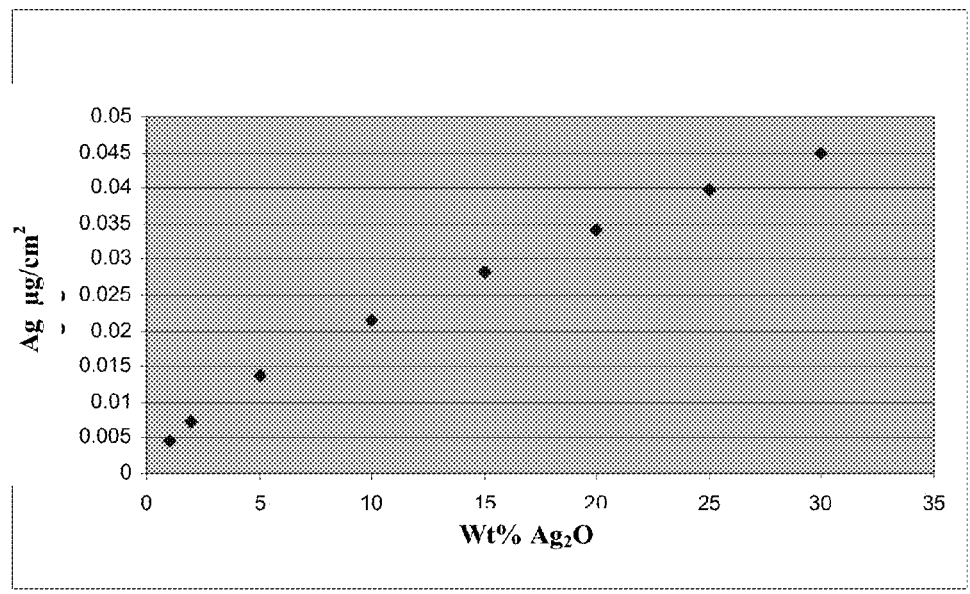

Using the EMP volume concentration estimates for various IOX schedules, one can make the graphs shown in FIGS. 6A and 6B. FIG. 6A, is a graph of the Ag-ion surface concentration in $ions/cm^2 \times 10^{14}$ versus the $Ag_2O$ concentration in wt %. One can also calculate the values of the surface concentration in $\mu g/cm^2$. The conversion of the estimates of surface concentration given above to units of $\mu g/cm^2$ allows comparison to some of the literature.

For the estimate from equation 1, one must use the $N/cm^2$ to convert to $\mu g/cm^2$ as shown in Equation 2.

$$\frac{\mu g}{cm^2} = \frac{N}{cm^2} \frac{1}{2} MWAg = (N/cm^2)(1.8 \times 10^{-22}) \qquad \text{Eq. 2}$$

Figure 8:
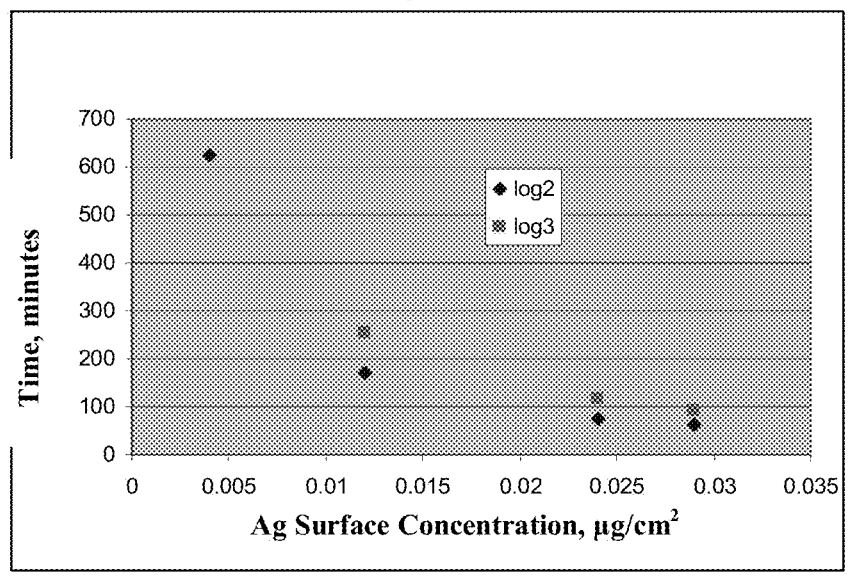
FIG. 8 is a graph of bacterial "kill" time versus surface Ag-ion concentration.

FIG. 6B, is the surface concentration expressed in $\mu g/cm^2$ vs. wt % $Ag_2O$ in the glass The 2-step method permits much higher $Ag^{+1}$ surface concentration to be achieved without any other undesirable effects. The very important and unique advantage of the higher surface concentration is the decrease in the bacteria "kill" time. This is the time that is required to produce a significant log reduction ≥2 as described below. FIG. 8 shows the dependence of the "kill" time as a function of the surface concentration using samples prepared by the 2-step method to have varying surface concentrations which were determined as described herein. The value of the "kill" time is a significant feature of the intended applications for all uses including hand-held device applications. It is only by using the 2-step method can one produce "kill" times of any practical utility as will be shown below, particularly for electronic devices colored cover or touch screen would impair the user's visual experience.

Figure 7:
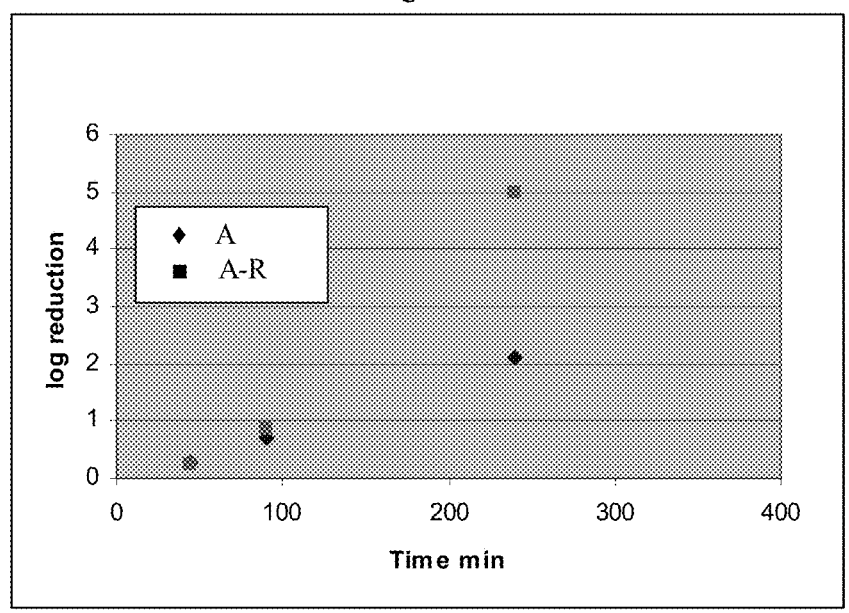
FIG. 7 is a graph comparing the antimicrobial activity, as log reduction versus time, for a silver ion containing glass as prepared by the 2-step method using a second IOX bath containing 0.15 wt % Ag.

It was further noted that the silver ion concentration increases as one goes further into the glass from the surface. While the origin of this phenomenon is uncertain, it was verified as real by a comparison of bacterial Log Reduction values as shown in FIG. 7 for a silver ion exchanged glass. FIG. 7 is a graph comparing the antimicrobial activity, as log reduction versus time, for a silver ion containing glass as prepared by the 2-step method using a second IOX bath containing 0.15 wt % Ag. Sample A (diamond ♦) represents the antimicrobial glass as prepared using the (0.15 wt % Ag bath, and Sample A-R (square ■) represents the same glass after the removal of 1 μm of the glass surface. The data of FIG. 7 indicate that the while Samples A and A-R have achieve substantially the same Log Reduction value during the during first approximately 100 minutes, after approximately 250 minutes the A-R Sample, which had the top 1 μm of glass removed, exhibited a much higher Log Reduction value. This illustrates that the Ag content actually increases as the distance from the surface increases and the importance of having as high a surface concentration as possible to maximize antimicrobial activity.

Antimicrobial Testing

Antibacterial tests were carried out using cultured gram negative *E. coli*; DH5alpha-Invitrogen Catalog No. 18258012, Lot No. 7672225, rendered Kanamycin resistant through a transformation with PucI9 (Invitogen) plasmid). The bacteria culture was started using either LB Kan Broth (Teknova #L8145) or Typtic Soy Broth (Teknova # T1550). Approximately 2 μl of liquid bacteria suspension or a pipette tip full of bacteria were streaked from an agar plate and dispensed into a capped tube containing 2-3 ml of broth and incubated overnight at 37° C. in a shaking incubator. The next day the bacteria culture was removed from the incubator and washed twice with PBS. The optical density (OD) was measured and the cell culture was diluted to a final bacterial concentration of approximately $1 \times 10^6$ CFU/ml. The cells were placed on the selected glass surface, antimicrobial or not antimicrobial (the control) for 6 hours at a temperature of 37° C. The buffers from each well were collected and the plates were twice washed with ice-cold PBS. For each well the buffer and wash were combined and the surface spread-plate method was used for colony counting.

Antimicrobial properties were exhibited in glass samples prepared using 1-step and 2-step methods. The control sample in all cases is an ion-exchanged glass that does not contain silver. Each of the glass samples was cut into a glass slide of 1×1 square inch (2.54 cm×2.54 cm square) and placed in a Petri dish. Three glass slides were used as negative controls. Gram negative E. coli bacteria were suspended in a ⅟500 LB medium at a concentration of $1 \times 10^6$ cells/ml. 156 µl of E. coli cell suspension was placed onto each sample surface and held in close contact by using a sterilized laboratory PARAFILM®, and incubated for 6 hours at 37° C. at saturation humidity (>95% relative humidity). Each sample was produced in triplicate. After 6 hours incubation, 2 ml of PBS buffer was added into each Petri dish. After shaking, both the slide and PARAFILM® were washed, and all the solution from each Petri dish was collected and placed onto a LB agar plate. After further 16-24 hour incubation at 37° C., the bacteria colony formation on the agar plate was examined. The results are shown by the bacterial growth response: Log reduction=$-\text{Log}(C_a/C_0)$, where $C_a$ is the concentration of bacteria (or virus or fungus) after exposure to the antimicrobial surface and $C_0$ is the concentration of bacteria of the control sample in which the bacteria is not in contact with an antimicrobial surface. As an example, a Log Reduction of 3=99.9% of bacterial or virus killed and a Log Reduction of 5=99.999% of bacteria or virus killed. The following Table 5 shows log reduction vs. surface Ag concentration.

For the purposes of the test and to insure that no bacterial contamination was initially present on the glass before the testing began, all the ion-exchanged glass samples, with or without silver, were sterilized by washing with 70 Vol. % ethanol for 1 minutes and wiped using distilled water. Table 5 show the results of bacterial testing results of glass samples after 6 hours using antimicrobial glass having surface silver ion concentrations, calculated as $Ag_2O$, as described in Table 5. The glasses in Table 5 were all prepared by the 2-step method. The first step IOX was carried out using a 100 wt % $KNO_3$ bath for a time in the range of 5-6 hours at a temperature of approximate 420°. The second step IOX was carried out using The surface $Ag^{+1}$ concentration, calculated in µg/cm², was determined as described herein

TABLE 5

Bacterial test: 2-Step Antimicrobial Glass Showing LR >5 After 6 Hours

| Sample, $Ag^{+1}$, µg/cm² | $2^{nd}$ Step IOX Conditions | Log Reduction |
|---|---|---|
| 0.0155 | 420° C., 5 minutes | >5 |
| 0.0155 | 420° C., 10 minutes | >5 |
| 0.016 | 420° C., 20 minutes | >5 |
| 0.03 | 420° C., 5 minutes | >5 |
| 0.0325 | 420° C., 10 minutes | >5 |
| 0.036 | 420° C., 20 minutes | >5 |

Table 6 Illustrates that the rate of bacterial reduction is faster for samples prepared using the 2-step method when compared to the 1-step method.

TABLE 6

Bacterial Test Results

| Time, minutes | 1-Step Method | 2-Step Method |
|---|---|---|
| 0 | 0 | 0 |
| 45 | 0.23 | 0.34 |

TABLE 6-continued

Bacterial Test Results

| Time, minutes | 1-Step Method | 2-Step Method |
|---|---|---|
| 90 | 2.95 | 3.7 |
| 180 | >5 | >5 |
| 270 | >5 | >5 |
| 360 | >5 | >5 |

Antiviral Test

An antiviral test was carried out using an Ag ion-exchanged glass having a surface ion concentration of 0.03 µg/cm² and HIV as the test virus. A Log Reduction of 2.22 was obtained after 1 hour.

Cytotoxicity Test

Cytotoxicity studies were conducted using NIH3T3 mouse fibroblast cells for culturing. Glass slides, 1×1 square inch (25.4 mm×25.4 mm), were attached to the bottom of a 96-well Holey plate. For the purposes of the test and to insure that no bacterial contamination was initially present on the glass before the cytotoxicity testing began, all the ion-exchanged glass samples, with or without silver, were sterilized by irradiation with UV light for 10-30 minutes, soaked in 70 Vol. % for 15 minutes and then wiped using distilled water. Four wells were cultured for each glass slide. The seeding density of each well was approximately $2 \times 10^4$ cells per well. After seeded wells were incubated for three days at 37° C. they were visually inspected using a live/dead stain and a fluorescence microscope for the counting of dead cells or colonies. No dead cells were observed for Samples C1, C2, C3 and C4 (Table 7).

TABLE 7

| Sample | Ag µg/cm² | Cytotoxicity |
|---|---|---|
| C0 | 0 | 0 = No cytotoxicity observed |
| C1 | 0.015 | 0 |
| C2 | 0.005 | 0 |
| C3 | 0.065 | 0 |
| C4 | 0.08 | 0 |

C0 = Control, IOXed aluminosilicate glass, No Ag
C1-C4 = prepared by the 2-step process as indicated; in µg/cm²

For use in hospitals and laboratories where mammalian cells infected with bacteria, viruses or fungi may be present, and coloring of the glass is not a consideration, higher concentrations of silver ions can be attained using the methods described herein.

Coatings

Another important aspect of the disclosure are the methods by which the antimicrobial behavior is maintained when selected functional coatings (including films) are placed on the surface of the antimicrobial, chemically strengthened glass. For example, in many touch screen applications (phones, computers, ATMs, etc) where the glass is used as a cover glass, a coating or film is placed on the glass surface so that fingerprints can be cleaned relatively easily. The coating(s) that facilitate cleaning are low surface energy coatings, for example, coatings in the class of "fluoroalkyl-silanes" of general formula $A_x\text{-Si}-B_{4-x}$, where A is selected from the group consisting of perfluoroalkyl $R_F-$, perfluoroalkyl terminated perfluoropolyether, perfluoroalkyl-alkyl, copolymers of fluoroalkene silanes and alkene silanes, and mixtures of fluoroalkylsilanes and hydrophilic silanes, B is Cl, acetoxy [$CH_3-C(O)-O-$] or alkoxy [for example $CH_3O-$ or $C_2H_5O-$], and x=1 or 2. Low surface energy coatings of the foregoing types are commercially available from different manufacturers, for example, Dow Corning, [DC2634-a perfluoropolyether silane in which the functional perfluoro moiety is Poly[oxy(1,1,2,2,3,3-hexafluoro-1,3-propanediyl)], α-(heptafluoropropyl)-ω-[1,1,2,2-tetra-fluoro-3-(2-propenyloxyl)propoxy]; Gelest [SIT8174.0, Tridecafluorotetrahydrooctyltrichlorosilane; SIT8371.0, Trifluoropropyltrichlorosilane; SIH5841.0 Heptadecafluorotetrahydrodecyl trichlorosilane; and SIH5841.0 (heptadecafluoro-1,1,2,2-tetrahydrodecyl)trichlorosilane; SIH5841.5 (heptadecafluoro-1,1,2,2-tetrahydrodecyl) trimethoxysilane; and SIH5841.2 (heptadecafluoro-1,1,2,2-tetrahydrodecyl)triethoxysilane]; Cytonix [FSM 1200 Perfluoropolyether mono-silane; FSD 2500 Medium molecular weight perfluoropolyether di-silane; FSD 4500 High molecular weight perfluoropolyether polysilanes]. The low surface energy coating should have a spacer or skeletal chain length in the range of 1 nm-20 nm, the skeletal chain being carbon atoms or a mixture of carbon and oxygen atoms in the case of the perfluoropolyethers. In one embodiment the chain length is in the range of 2 nm to 20 nm. In a further embodiment the chain length is in the range of 1-10 nm. Other examples are (a) copolymers of fluoroalkene silanes and alkene silanes; and
(b) mixtures of fluoroalkylsilanes and hydrophilic silanes.

Silanes other than the foregoing can also be used provided that they do not prevent water vapor from reaching the surface of the glass so that silver ions can be transported from the glass surface to the microbe to thereby kill the microbe or inhibit its growth.

Generally, the fluoro-containing coatings describe above have 1 or 2 fluorocarbon-containing moieties attached to the silicon and each of the moieties, independently, have a chain length in the range of 1 nm to 20 nm, and the chain may include oxygen atoms or sulphur atoms along the chain. In one embodiment the chain length is in the range of 2 nm to 20 nm. In a further embodiment the chain length is in the range of 1-10 nm. What is important for the coating is that at least part the fluorocarbon moiety be sufficiently distant from the surface so that water molecules can come into contact with the surface, pick up silver ions on the surface, and transport the silver ions to a microbe where they can be absorbed in to microbe and thus kill it or decrease its reproductive rate. Consequently, it is preferred that one or two fluorocarbon moieties be attached to the silicon atom and that the silicon atom be bonded to the glass by two or three Si—O bonds. For example, if the alkyl group of (a) above, which functions as a spacer or skeletal chain between the silver-containing glass surface and the fluorocarbon moiety, is too short, then hydrophobic fluorocarbon moiety can block water molecules from reaching the glass surface and thus silver ions cannot be transported from the surface to and into the microbe. In another instance, without being held to any particular theory, it is believed that the oxygen atoms in a perfluoropolyether alkoxy silane that has been bonded to the surface of the antimicrobial glass can facilitate the migration of water molecules by oxygen atoms along the chain to the surface where the water molecules can coordinate to silver ions and facilitate the ions transport to the microbe. An exemplary perfluoropolyether alkoxy silane is Dow Corning® 2634 used as 0.02-1 wt % solutions in a fluorinated solvent. After the coating material was applied to the antimicrobial glass article such as described herein, the coating was cured to adhere the coating to the surface of the glass article and finally sonicated in a fluorinated solvent (for example, Novec™ HFE7200, 3M Company) bath for a 3 minutes remove any unreacted coating material. The curing was done thermally by either heating the coated in an oven, for example, at 50° C., 50% RH, for a cure time as suggested by the manufacturer or by infrared heating of the coated articles. The coated article was then heated in an oven for a time in the range of 30 minutes to 2 hours to cure the coating material to the glass surface.

Figure 2:
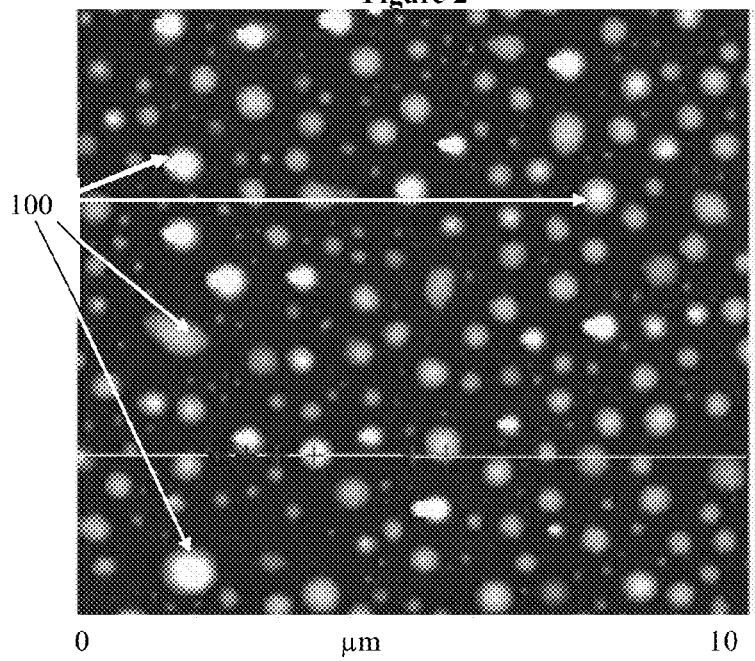
FIG. 2 is an SEM micrograph of the surface of a chemically strengthened, silver ion containing antimicrobial glass coated with a low surface energy coating, the micrograph showing the domains of the coating material as dots of varying size on the surface of the glass.

The method and process for the deposition of these coatings is capable of controlling the thickness and morphology of the coating on the surface of the glass. Process methods and steps can be introduced where the coating was deposited in such a fashion either to be discontinuous or quasi-discontinuous. Such process methods include, but are not limited to, vapor deposition or spray coating through a predetermined coverage mask, ink jet printing, micro contact printing using a master which would allow the fluorosilane to be coated in specific regions, humidity curing to allow phase separation of the fluorosilane. When the coating is sufficiently thin it can be continuous. Thin continuous coatings can be deposited, for example, by dip, spray and vapor deposition followed by curing to adhere the silanes, and followed by ultrasound cleaning to remove un-reacted but physically adsorbed silanes. The foregoing procedures allow the antimicrobial action to persist in open uncoated areas, or in areas where the coating is very thin or the surface is coating-free while at the same time maintaining intended functional performance of the coating. FIG. 2 is an AFM (atomic force micrograph) illustrating this desired morphology in the form of localized domains (islands-in-the-sea) of fluorosilane deposited on the surface of a silver ion containing, chemically strengthened glass as described herein. In FIG. 2 the glass (or sea) is the black background and the coating domains or islands 100 are shown as the white to gray dots or ovals of various sizes that are dispersed on the background. In the case where the coating is continuous, the coating is relatively thin, having a thickness, in one embodiment, in the range of 0.5 nm to 20 nm in order for the antimicrobial activity of the glass surface to remain effective. In another embodiment the thickness of the coating is in the range of 0.5 nm to 5 nm. In a further embodiment the thickness of the coating is in the range of 1 nm to 3 nm. In the thin coating case a mixed self-assembled monolayer can be prepared on the surface using two silanes, where one silane is a fluoroalkylsilane and the other silane is a hydrophilic silane (for example, a polyethylene glycol containing silane), wherein the hydrophilic or "water loving" silane domains assist in the antimicrobial action by capturing water molecules and presenting them to the surface where the water can pick up silver ions for transport to the microbe. In one embodiment fluoro-oligoethylene glycol silanes can also be used, where the oligoethylene glycol part of the silanes can assist in capturing free water at the interface.

Figure 3:
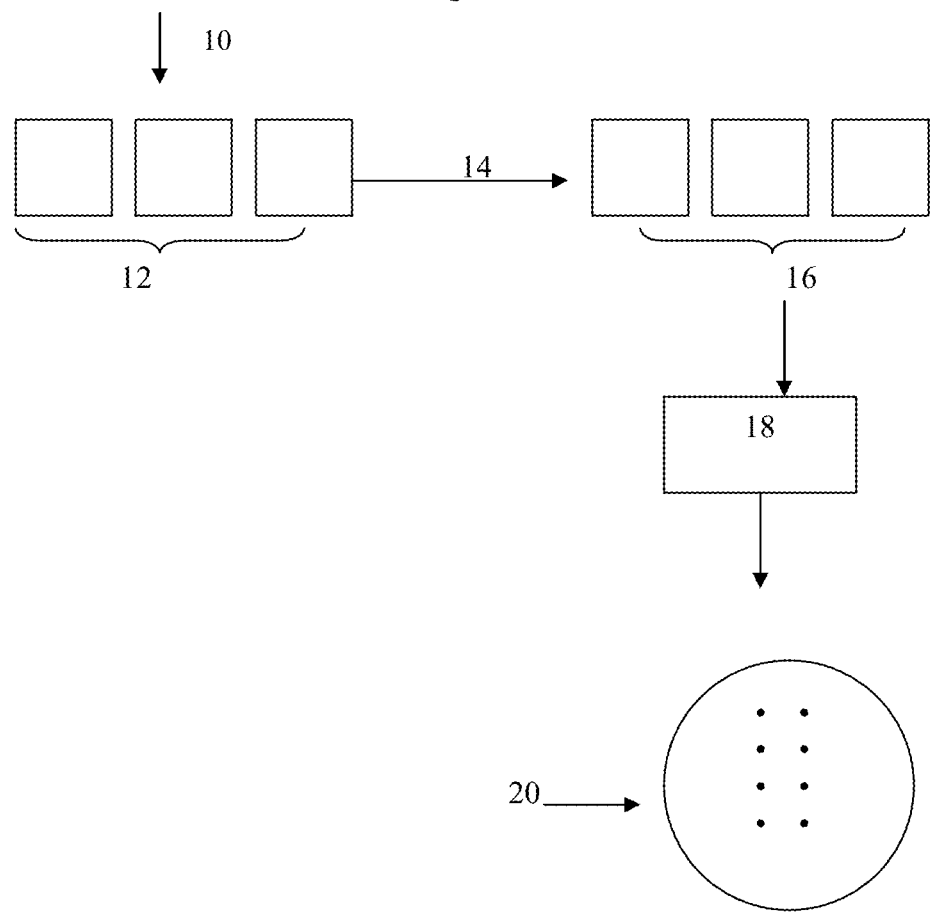
FIG. 3 is a schematic diagram of the modified JISZ 2801: 2000 method used for evaluating the antibacterial properties of silver-containing glass having a hydrophobic coating on their surface.

The test method used for determining antibacterial properties of a silver-containing glass having a hydrophobic coating thereon was a modified version of the JISZ-2801: 2000 method, which is a Japanese Industrial Standard that was developed to measure the antibacterial activity of hydrophobic materials, particularly polymers into which silver ions had been incorporated. The antibacterial activity is measured by quantitatively by determining the survival of bacteria cells that have been held in intimate contact with a surface thought to be antibacterial and incubated for 24 hours at 35° C. After the time period has elapsed the cells are counted and compared to a non-treated surface. The test was modified in that for the incubation period was changed to 6 hours at 37° C. After 6 hours the samples were removed from the incubator and the entire testing surface was thoroughly washed with PBS to ensure that all bacteria were removed. The cells and the PBS wash were then transferred to a broth agar plate for overnight culture. After a period of 16-24 hours the bacterial colonies on the agar plate were counted. FIG. 3 is a diagram illustrating the modified method that was used. In FIG. 3 numeral 10 represents the addition of a 400 µl bacterial suspension of concentration 1×10$^6$ cells/ml to the sample plates 12 which can be either a Ag-containing glass plate or a control (no Ag) plate, covering 14 the plates having a bacterial suspension thereon with the PARAFILM® resulting in PARAFILM® covered plates 16, and thereafter incubating the bacteria at 37° C. for 6 hours as indicated by 18, and lastly counting the colonies as represented by 20. The samples were tested using *E. coli* (gram negative) bacteria.

Table 8 presents *E. coli* antibacterial results obtained using 2-step Ag ion exchanged glass with varying surface concentrations followed by a deposition of the coating. The Control Sample was ion-exchanged using a 100% KNO$_3$ bath (no AgNO$_3$). The coating material was a fluorosilane which was applied to a thickness in the range of 0.5 nm to 5 nm and was uniform across the surface of the glass. After coating the samples were cured to adhere the silane to the surface of the glass article and finally sonicated in a fluorinated solvent bath to remove unreacted silanes.

TABLE 8

| Sample | IOX Bath | % reduction | Time, hours |
| --- | --- | --- | --- |
| S10-NC | Control, 100% KNO$_3$ | 0 | NA |
| S10-C | Control, 100% KNO$_3$ | 0 | NA |
| S12-NC | 0.015 ug/cm2 | 99.9 | ≥3 |
| S13-C | 0.015 ug/cm2 | 99.9 | ≥3 |
| S14-NC | 0.033 ug/cm2 | 99.9 | ≤2 |
| S14-C | 0.033 ug/cm2 | 99.9 | ≤2 |

S10 is the control sample.
NC = no coating
C = coated
Bacterial suspension was *E. coli* prepared as previously described. Coating was a hydrophobic coating material of less than 20 nm thickness. The tests were repeated twice from the start and produced the same results.

There is minimal impact on the compressive stress using the 2-step method, because the depth of the Ag ion exchange into the glass in the second step is so shallow, the compressive stress of the glass, which was chemically strengthened in a first step by ion-exchange of larger ions, typically potassium or larger alkali metal ions, for smaller ions in the glass as prepared, typically sodium and lithium ions, the compressive stress of the glass is not measurably affected. Further, it is noted that the ionic radius of silver and potassium ions are substantially the same, the Pauling ionic radii of silver and potassium being 1.26 and 1.33 Angstroms, respectively. Consequently, an ion-exchange of silver ions for potassium ions already in the glass after the first step ion-exchange will have a minimal effect on the compressive stress of the glass. Table 9 compares the compressive stress of the glass samples after the first the first ion-exchange step, KNO$_3$ exchange only, and after the second ion-exchange step using a bath containing both AgNO$_3$ and KNO$_3$. The samples were tested using the Ring-on-Ring test both before and after abrasion. The values in Table are the average of 3-4 sample tests and the standard deviation is given. Samples were prepared using the 2-step ion-exchange method described herein. The first step ion-exchange was carried out for 5.5 hours using a 100% KNO$_3$ bath at 420° C. A plurality of samples was set aside after the first ion-exchange step was completed. The remainder of the samples were then subjected to the second ion-exchange step for 20 minutes using a 5 wt % AgNO$_3$/95 wt % KNO$_3$ at 420°

TABLE 9

| Sample | Step 1 KNO$_3$ | Step 2 AgNO$_3$/KNO$_3$ | Before Abrasion MPa | SD MPa | After Abrasion MPa | SD MPa |
| --- | --- | --- | --- | --- | --- | --- |
| 1 | Yes | No | 970 | ±90 | | |
| 2 | Yes | Yes | 800 | ±260 | — | — |
| 1A | Yes | No | — | — | 380 | ±40 |
| 2A | Yes | Yes | — | — | 400 | ±40 |

Samples 1 and 2 results are samples as-made and before abrasion.
Samples 1A and 2A results are for samples after abrasion.
SD = Standard Deviation The results shown in Table 9 indicate that the second ion-exchange step with the AgNO$_3$/KNO$_3$ has a minimal effect on the compressive stress.

In an additional embodiment the disclosure is to a method of making an antimicrobial, chemically strengthened glass article, said method comprising providing glass article having a first surface, a second surface and a selected thickness between said surfaces, and alkali metal ions in the glass; providing a first ion-exchange bath consisting of at least one alkali metal ion larger that the alkali metal ions in the provided glass to impart a compressive stress greater than 500 MPa into the glass; providing a second ion-exchange bath consisting essentially of 0.005 wt % to 5.0 wt % silver nitrate, the remainder of the bath consisting of the at least one of the alkali metal ions in the first bath; ion-exchanging with the second bath to thereby incorporate said silver and said alkali metal ion(s) into at least one of said surfaces to form a glass article having a compressive stress of greater than 250 MPa and at least one an antimicrobial, chemically strengthened surface; and the concentration of silver ion on the surface of the glass is in the range of greater than zero to less than 0.047 µg/cm$^2$.

Thus, in one embodiment the disclosure is to an antimicrobial, chemically strengthened glass comprising a glass article having a compressive stress layer extending from the surface of the glass to a selected depth in the glass; an antimicrobial Ag+ region that is part of the compressive stress layer of the glass article; wherein the compressive stress in the glass is at least 250 MPa and the surface concentration of the Ag$^{+1}$ ion is in the range of greater than zero to less than or equal to 0.047 µg/cm$^2$. The glass further comprises a low surface energy coating on the surface of the glass having the characteristic of allowing water molecules to reach the Ag+ ions in the glass. The glass is capable of inhibiting at least 2 microbes species to a Log Reduction greater that 1 within 1 hour. In an embodiment the glass has an antibacterial Log Reduction of greater than 4 after 6 hours. In another embodiment the glass has an antibacterial Log Reduction of greater than 5 after 6 hours. In a further embodiment the glass has an Ag$^{+1}$ ion surface concentration in the range of 0.005 µg/cm$^2$ to 0.035 µg/cm$^2$ and is non-cytotoxic. In an additional embodiment the glass has an Ag$^{+1}$ ion surface concentration in the range of 0.01 µg/cm$^2$ µg/cm$^2$ to 0.035 µg/cm$^2$ and is non-cytotoxic. In an embodiment the glass has an Ag$^{+1}$ ion surface concentration in the range of 0.015 µg/cm$^2$ µg/cm$^2$ to 0.030 µg/cm$^2$ and is non-cytotoxic. In another embodiment the compressive stress is at least 500 MPa. In an additional embodiment the compressive stress is at least 600 MPa. The low surface energy functional coating has a terminal perfluorinated moiety and is selected from the group consisting of silanes of general formula $A_x$-Si—$B_{4-x}$, where A is perfluoroalkyl $R_F$—, perfluoroalkyl terminated perfluoropolyether, perfluoroalkyl-alkyl, copolymers of fluoroalkene silanes and alkene silanes, and mixtures of fluoroalkylsilanes and hydrophilic silanes, B is Cl, acetoxy [$CH_3$—C(O)—O-] or alkoxy, and x=1 or 2; and the coating has thickness in the range of 0.5 nm to 20 nm and is bonded to the surface of the glass by at least one SiO bond between the coating silicon atom and an glass oxygen atom. The coating has a skeletal chain length from the silicon atom to its end, for example, a final $CF_3$ moiety, that is in the range of 2 nm to 20 nm, the skeletal chain consisting of at least one selected from the group consisting of (a) carbon atoms and (b) a combination of carbon and oxygen atoms in the case of polyethers. In an embodiment the coating is a perfluoroalkyl alkoxy silane of formula $(R_{F1})_x$—$Si(OR)_{4-x}$, where x=1 or 2, $R_{F1}$ moiety is a perfluoroalkyl group having a carbon chain length in the range of 2 nm to 20 nm and OR is acetoxy, —$OCH_3$ or $OCH_2H_3$. In another embodiment the coating is $(RO)_{4-z}$—Si—$[(CH_2)_3$—$OCF_2$—$CF_2$—$[OCF_2$—$CF_2$—$CF_2]_n$—$F]_z$, where z=1 or 2, n is an integer sufficient to provide that $[(CH_2)_3$—$OCF_2$—$CF_2$—$[OCF_2$—$CF_2$—$CF_2]_n$—F] has a chain length in the range of 2 nm to 20 nm, and RO=$CH_3O$—, $CH_3$—$CH_2O$—, or $CH_3C(O)O$—. In a further embodiment the coating is a perfluoroalkyl alkyl alkoxy silane of formula $RO)_{4z}$—Si—$[(CH_2)_x$—$(CF_2)_y CF_3]_z$, where x+y are integers whose sum is sufficient to provide that $[(CH_2)_x$—$(CF_2)_y$—$CF_3]$ has a length in the range of 2 nm to 20 nm, with the provision that y≥x, z is 1 or 2, and RO=$CH_3O$—, $CH_3$—$CH_2O$—, or $CH_3C(O)O$—.

According to an embodiment, an antimicrobial glass is provided that includes a glass article having a surface; an antimicrobial Ag+ region extending from the surface of the glass article to a depth in the glass article, the antimicrobial Ag+ region having a plurality of $Ag^{+1}$ ions, and an ion exchange-derived, compressive stress layer having a compressive stress of at least 200 MPa. Further, the concentration of the plurality of $Ag^{+1}$ ions within 20 nm from the surface of the glass article is in the range of greater than or equal to 0.015 μg/cm$^2$ to less than or equal to 0.08 μg/cm$^2$ as measured by x-ray photoluminescence spectroscopy (XPS) or electron microprobe (EMP) analytical techniques. In addition, such an antimicrobial glass can be produced by creating a compressive stress in an outer region using an ion-exchange bath consisting essentially of potassium nitrate and a selected amount of sliver nitrate to strengthen the glass to impart antimicrobial properties to the glass, the outer region extending from the surface to a depth of layer (DOL), wherein the compressive stress is at least 200 MPa and the DOL that is under compression due to $K^{+1}$+$Ag^{+1}$ is at least 50 μm, and the DOL of the $Ag^{+1}$ ion is at least 30 μm. Further, a DOL of up to approximately 150 μm with a peak Ag content (as the oxide) of approximately 6.0 wt % at the surface of the glass and approximately 0.5 wt % at 125 μm and 0.1 wt % at 150 μm can be obtained in some implementations. As shown in FIG. 6B, a peak content of approximately 6.0 wt % of $Ag_2O$ correlates to greater than or equal to 0.015 μg/cm$^2$ of Ag ions.

In an embodiment the antimicrobial, chemically strengthened glass is selected from the group consisting of an antimicrobial, chemically strengthened alkali aluminosilicate glass and an alkali aluminoborosilicate glass, and the glass has a silver ion surface concentration in the range of 0.01 μg/cm$^2$ and 0.035 μg/cm$^2$, and the glass surface is not cytotoxic. In an embodiment the transmission of the glass, uncorrected for reflection losses, over the wavelength range of 400 nm to 750 nm is at least 88%. In another embodiment the ratio of the transmission at 428 nm/650 nm is at least 99%.

In addition the disclosure is thus further directed to a method of making an antimicrobial, chemically strengthened glass article comprising providing glass article having a first surface, a second surface and a selected thickness between said surfaces, and alkali metal ions in the glass; providing a first ion-exchange bath consisting of at least one alkali metal ion larger that the alkali metal ions in the provided glass to impart a compressive stress greater than 250 MPa into the glass; providing a second ion-exchange bath consisting essentially of 0.005 wt % to 5.0 wt % silver nitrate, the remainder of the bath consisting of the at least one of the alkali metal ions in the first bath; ion-exchanging with the second bath to thereby incorporate said silver and said alkali metal ion(s) into at least one of said surfaces to form a glass article having a compressive stress of greater than 250 MPa and at least one an antimicrobial, chemically strengthened surface; and wherein the concentration of silver ion on the surface of the glass is in the range of greater than zero to less than 0.047 μg/cm$^2$ and the second bath ion-exchange time is less than 30 minutes. In one embodiment the compressive stress is greater than 500 MPa. The second ion-exchange bath consists of silver nitrate in an amount in the range of 0.15 wt % to 10 wt %, and the remainder of the bath is potassium nitrate. In one embodiment the second bath ion exchange time is less than or equal to 20 minutes. In another embodiment the second bath ion exchange time is less than or equal to 10 minutes. The provided glass article is selected from the group consisting of soda lime glass, alkali aluminosilicate glass and alkali aluminoborosilicate glass articles. In one embodiment the provided glass is selected from glasses having a composition:

(a) 60-70 mol % $SiO_2$; 6-14 mol % $Al_2O_3$; 0-15 mol % $B_2O_3$; 0-15 mol % $Li_2O$; 0-20 mol % $Na_2O$; 0-10 mol % $K_2O$; 0-8 mol % MgO; 0-10 mol % CaO; 0-5 mol % $ZrO_2$; 0-1 mol % $SnO_2$; 0-1 mol % $CeO_2$; less than 50 ppm $As_2O_3$; and less than 50 ppm $Sb_2O_3$; wherein 12 mol %≤$Li_2O$+$Na_2O$+$K_2O$≤20 mol % and 0 mol %≤MgO+CaO≤10 mol %;

(b) 64 mol %≤$SiO_2$≤68 mol %; 12 mol %≤$Na_2O$≤16 mol %; 8 mol %≤$Al_2O_3$≤12 mol %; 0 mol %≤$B_2O_3$≤3 mol %; 2 mol %≤$K_2O$≤5 mol %; 4 mol %≤MgO 6 mol %; and 0 mol %≤CaO≤5 mol %, and wherein 66 mol %≤$SiO_2$+$B_2O_3$+CaO≤69 mol %; $Na_2O$+$K_2O$+$B_2O_3$+MgO+CaO+SrO>10 mol %; 5 mol %≤MgO+CaO+SrO≤8 mol %; ($Na_2O$+$B_2O_3$)–$Al_2O_3$≤2 mol %; 2 mol %≤$Na_2O$–$Al_2O_3$≤6 mol %; and 4 mol %≤($Na_2O$+$K_2O$)–$Al_2O_3$≤10 mol %;

(c) 61 mol %≤$SiO_2$≤75 mol %; 9 mol %≤$Na_2O$≤21 mol %; 7 mol %≤$Al_2O_3$≤15 mol %; 0 mol %≤$B_2O_3$≤12 mol %; 0 mol %≤$K_2O$≤4 mol %; 0 mol %≤MgO≤7 mol %; and 0 mol %≤CaO≤mol %;

(d) 50 mol %≤$SiO_2$≤70 mol %; 8 mol %≤$Na_2O$≤16 mol %; 9 mol %≤$Al_2O_3$≤17 mol %; 2 mol %≤$B_2O_3$≤12 mol %; 0 mol %≤$K_2O$≤4 mol %; 0 mol %≤MgO≤4 mol %; and 0 mol %≤CaO≤0.2 mol %. wherein the alkali metal oxides and the alkaline earth metal oxides are modifiers and the ratio [(mol %≤$Al_2O_3$+mol % $B_2O_3$)÷Σ mol %≤modifiers] is greater than 1, that is:

[(mol % $Al_2O_3$+$B_2O_3$)÷Σmol %≤modifiers]>1; and (e) $SiO_2$>50 mol %; 11 mol %≤$Na_2O$≤25 mol %; 7 mol %≤$Al_2O_3$≤26 mol %; o mol %≤$B_2O_3$≤9 mol %; 0 mol %≤K$_2$O≤2.5 mol %; 0 mol %≤MgO≤8.5 mol %; and 0 mol %≤CaO≤1.52 mol %; wherein the foregoing are substantially lithium free.

The method further comprises the step of applying a low surface energy coating to said at least one antimicrobial, chemically strengthened glass surface, the coating being selected from the group consisting of fluoroalkylsilanes, perfluoropolyether alkoxy silanes, perfluoroalkyl alkoxy silanes, fluoroalkylsilane-(non-fluoroalkylsilane) copolymers, and mixtures of fluoroalkylsilanes and hydrophilic silanes; and curing the applied coating to thereby bond the coating to the glass by a Si—O bond between the coating and the glass; wherein the functional coating has a thickness in the range of 0.5 nm to 20 nm. In one embodiment the low surface energy functional coating is a perfluoroalkyl alkoxy silane of formula $(R_{F1})_x$—$Si(OR)_{4-x}$, where x=1 or 2, $R_{F1}$ moiety is a perfluoroalkyl group having a carbon chain length in the range of 16-130 carbon atom and OR is acetoxy, —OCH$_3$ or OCH$_2$H$_3$. In another embodiment the low surface energy functional coating bonded to the antimicrobial, chemically strengthened glass is a perfluoropolyether alkoxy silane of formula $[CF_3$—$(CF_2CF_2O)_a]_x$—$Si(OR)_{4-x}$ where a is in the range of 5-10, x=1 or 1, and OR is acetoxy, —OCH$_3$ or OCH$_2$H$_3$, wherein the total perfluoroether chain length from the silicon atom to the end of the chain at its greatest length its end is in the range of 1 nm to 10 nm, 16 to 130 atoms. In a further embodiment the low surface energy functional coating bonded to the antimicrobial, chemically strengthened glass is a perfluoroalkyl alkyl alkoxy silane of formula $[R_{F2}$—$(CH_2)_b]_x$—$Si(OR)_{4-x}$ where $R_{F2}$ is a perfluoroalkyl group having a carbon chain length in the range of 10-16 carbon atoms, b is in the range of 14-20, x=2 or 3 and OR is acetoxy, —OCH$_3$ or OCH$_2$CH$_3$. In one embodiment the low surface energy functional coating is applied to form domains on the surface of the glass and a non-domain area without coating. In another embodiment the low surface energy applied uniformly/continuously across the glass surface and has a thickness in the range of 0.5 nm to 10 nm. In one embodiment the thickness in the range of 1 nm to 3 nm. The method produces as glass having a transmission of the glass, uncorrected for reflection losses, over the wavelength of 400 nm to 750 nm is at least 88%., and also the ratio of the transmission at 428 nm/650 nm is 99%.

For use as antimicrobial shelving, table tops and other applications in hospitals, laboratories and other institutions handling biological substances, where color in the glass is not a consideration, glass having a silver ion surface concentration of greater than 0.035 μg/cm$^2$ may be suitable. Glass having a silver ion surface concentration of 0.5 or higher may be prepared using the methods described herein.

While typical embodiments have been set forth for the purpose of illustration, the foregoing description should not be deemed to be a limitation on the scope of the disclosure or the appended claims. Accordingly, various modifications, adaptations, and alternatives may occur to one skilled in the art without departing from the spirit and scope of this disclosure or the appended claims.

We claim:

1. An antimicrobial glass comprising:
a glass article having a surface;
an antimicrobial Ag+ region extending from the surface of the glass article to a depth in the glass article, the antimicrobial Ag+ region having a plurality of Ag$^{+1}$ ions; and an ion exchange-derived, compressive stress layer having a compressive stress of at least 200 MPa,
wherein the concentration of the plurality of Ag$^{+1}$ ions within 20 nm from the surface of the glass article is in the range of greater than or equal to 0.015 μg/cm$^2$ to less than or equal to 0.08 μg/cm$^2$ as measured by x-ray photoluminescence spectroscopy (XPS) or electron microprobe (EMP) analytical techniques.

2. The antimicrobial glass of claim 1, wherein the compressive stress layer has a compressive stress of at least 250 MPa.

3. The antimicrobial glass of claim 1, wherein the glass is colorless.

4. The antimicrobial glass of claim 1, wherein the depth of the antimicrobial Ag+ region is about 20 μm or less from the surface.

5. The antimicrobial glass of claim 1, wherein the concentration of the plurality of Ag$^{+1}$ ions is about 3.22 atomic % or less extending from the surface of the glass article to a depth of about 5 nm.

6. The antimicrobial glass of claim 1, wherein the depth of the antimicrobial Ag+ region is about 1 μm or less from the surface.

7. The antimicrobial glass of claim 1, wherein the concentration of the plurality of Ag$^{+1}$ ions within 20 nm from the surface of the glass article is in the range of greater than or equal to 0.015 μg/cm$^2$ to less than or equal to 0.05 μg/cm$^2$.

8. The antimicrobial glass of claim 1, further comprising a hydrophobic coating.

9. The antimicrobial glass of claim 8, wherein the hydrophobic coating has a thickness in the range from about 0.5 nm to about 20 nm.

10. The antimicrobial glass of claim 8, wherein the hydrophobic coating comprises one of a discontinuous coating and a continuous peak-to-valley coating, and wherein the continuous peak-to-valley coating comprises at least one peak having a first thickness and at least one valley having a second thickness less than the first thickness.

11. The antimicrobial glass of claim 1, wherein the composition of the glass article is selected from the group consisting of soda lime glass, alkali aluminosilicate glass and alkali aluminoborosilicate glass.

12. A device comprising the glass article of claim 1.

13. The device of claim 12, wherein the device comprises an ATM, a touch screen computer, a cellphone, or an electronic book reader.

14. An antimicrobial glass comprising:
a glass article having a surface;
an antimicrobial Ag+ region extending from the surface of the glass article to a depth of region in the glass article, the antimicrobial Ag+ region having a plurality of Ag$^{+1}$ ions,
wherein the concentration of the plurality of Ag$^{+1}$ ions within 20 nm from the surface of the glass article is in the range of greater than or equal to 0.015 μg/cm$^2$ to less than or equal to 0.08 μg/cm$^2$ as measured by x-ray photoluminescence spectroscopy (XPS) or electron microprobe (EMP) analytical techniques,
wherein the antimicrobial Ag+ region comprises a concentration of Ag$_2$O of up to about 25 wt % from the surface of the glass article, and
wherein the antimicrobial glass has a strength of at least 380 MPa based on a Ring on Ring test conducted after abrasion of the surface.

15. The antimicrobial glass of claim 14, wherein the concentration of Ag$_2$O is up to about 19 wt %.

16. The antimicrobial glass of claim 14, wherein the depth of region is up to about 20 μm.

17. A device comprising the glass article of claim 14.

18. The device of claim 17, wherein the device comprises an ATM, a touch screen computer, a cellphone, or an electronic book reader.

19. The device of claim 17, wherein the glass article further comprises a hydrophobic coating.

\* \* \* \* \*

UNITED STATES PATENT AND TRADEMARK OFFICE
CERTIFICATE OF CORRECTION

PATENT NO. : 9,609,873 B2
APPLICATION NO. : 14/590242
DATED : April 4, 2017
INVENTOR(S) : Nicholas Francis Borrelli et al.

It is certified that error appears in the above-identified patent and that said Letters Patent is hereby corrected as shown below:

On the Title Page

On the page 2, in Column 2, under item (56) "Other Publications", Line 19, delete "Biocompativle" and insert -- Biocompatible --.

On the page 2, in Column 2, under item (56) "Other Publications", Line 22, delete "Seige" and insert -- Siege --.

In the Specification

In Column 1, Line 18, before "relied" delete "s".

In the Claims

In Column 21, Line 67, in Claim 1, delete "laver" and insert -- layer --.

Signed and Sealed this
Twenty-ninth Day of October, 2024

Katherine Kelly Vidal
*Director of the United States Patent and Trademark Office*